US006112224A

United States Patent [19]
Peifer et al.

[11] Patent Number: 6,112,224
[45] Date of Patent: Aug. 29, 2000

[54] PATIENT MONITORING STATION USING A SINGLE INTERRUPT RESOURCE TO SUPPORT MULTIPLE MEASUREMENT DEVICES

[75] Inventors: John W. Peifer; Andrew Hopper, both of Atlanta; Michael Burrow; Barry Sudduth, both of Lawrenceville; Samir Panchal, Norcross; Andy Quay, Kennesaw; W. Edward Price, Smyrna, all of Ga.

[73] Assignee: Georgia Tech Research Corporation, Atlanta, Ga.

[21] Appl. No.: 08/934,442

[22] Filed: Sep. 19, 1997

Related U.S. Application Data
[60] Provisional application No. 60/026,986, Sep. 20, 1996.

[51] Int. Cl.⁷ .............................. G06F 13/00; G06F 15/00
[52] U.S. Cl. .......................... 709/202; 709/201; 709/225; 709/229; 709/242; 340/825.06; 340/825.55; 364/200; 364/132; 364/8; 364/DIG. 1; 710/47
[58] Field of Search ..................... 128/671, 903, 128/670, 96, 700, 715, 701, 782; 364/200, 133, 8, DIG. 1; 340/825.05, 825.06, 55; 395/736, 733, 739, 741, 742, 868; 709/225, 201, 202, 229, 238, 239, 242, 218, 217, 3; 710/47

[56] References Cited

U.S. PATENT DOCUMENTS

| | | | |
|---|---|---|---|
| 4,259,548 | 3/1981 | Fahey et al. ........................... | 179/5 R |
| 4,740,882 | 4/1988 | Miller ..................................... | 364/132 |
| 4,768,149 | 8/1988 | Konopik et al. ........................ | 364/200 |
| 4,838,275 | 6/1989 | Lee ........................................ | 128/670 |
| 5,339,821 | 8/1994 | Fujimoto ................................ | 128/700 |
| 5,375,604 | 12/1994 | Kelly et al. ............................ | 128/671 |
| 5,434,611 | 7/1995 | Tamura .................................... | 348/8 |
| 5,438,607 | 8/1995 | Przygoda, Jr. et al. ................. | 379/38 |
| 5,441,047 | 8/1995 | David et al. ........................... | 128/670 |
| 5,502,726 | 3/1996 | Fischer .................................. | 370/94.1 |
| 5,544,649 | 8/1996 | David et al. ........................... | 128/630 |
| 5,553,609 | 9/1996 | Chen et al. ............................ | 128/630 |
| 5,558,638 | 9/1996 | Evers et al. ............................ | 604/66 |
| 5,576,952 | 11/1996 | Stutman et al. ..................... | 364/413.02 |

Primary Examiner—Frank J. Asta
Assistant Examiner—Beatriz Prieto
Attorney, Agent, or Firm—Thomas, Kayden, Horstemeyer & Risley

[57] ABSTRACT

A patient monitoring system for use in a telemedicine system that allows multiple medical devices to communicate with a control unit via an interface that uses a single interrupt. In architecture, the system can be implemented in hardware, or a combination of hardware and software, and is more particularly implemented as follows: A plurality of medical devices are connected to a control unit via a device interface that uses a single interrupt in the transmission of data from the medical devices to the control unit. When a medical device has data to transmit to the control unit, the medical device transmits data to the device interface, and the device interface uses its single interrupt line in the transmission of data to the control unit.

25 Claims, 4 Drawing Sheets

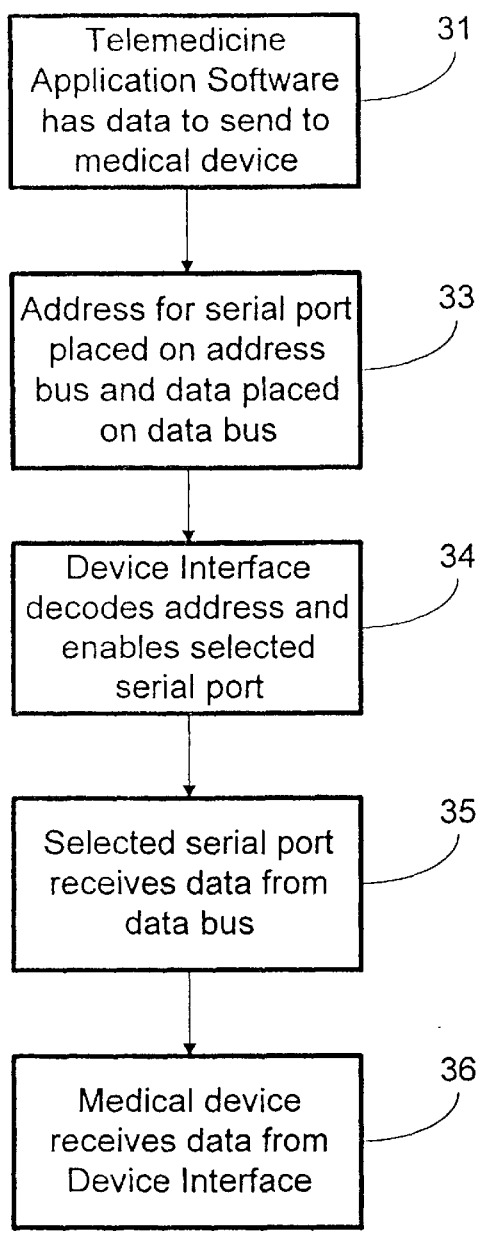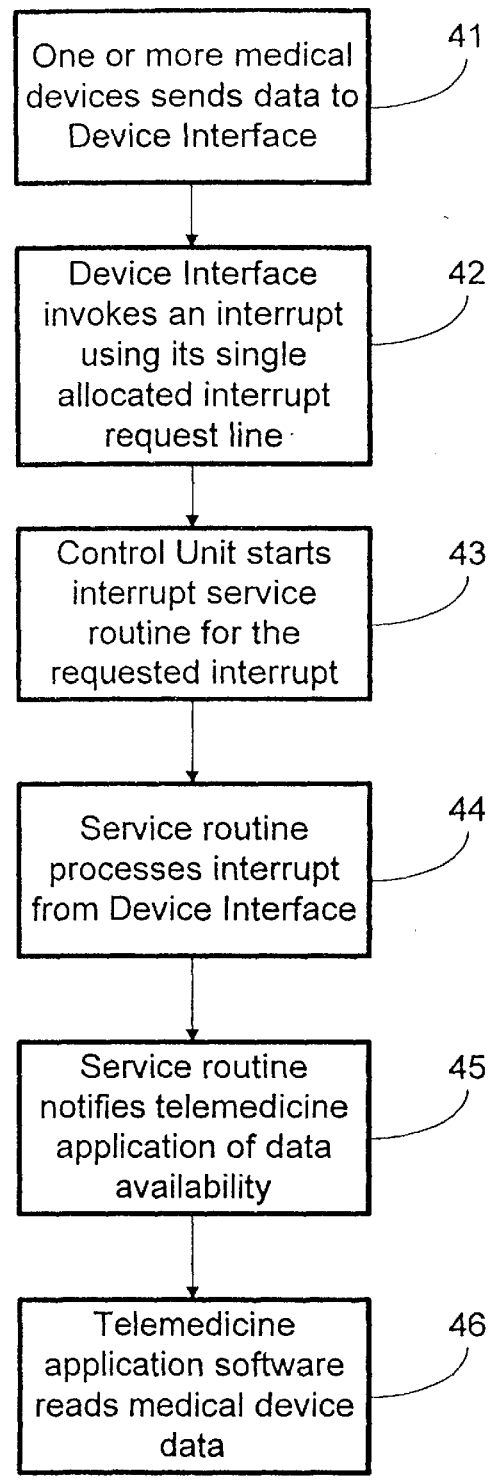
Fig. 4
Fig. 5

PATIENT MONITORING STATION USING A SINGLE INTERRUPT RESOURCE TO SUPPORT MULTIPLE MEASUREMENT DEVICES

CROSS REFERENCE TO RELATED APPLICATION

This application claims priority to and the benefit of the filing date of U.S. Provisional application Ser. No. 60/026,986 (Attorney Docket Number 62002-8450), filed Sep. 20, 1996, entitled ELECTRONIC HOUSE CALL SYSTEM. The above referenced provisional application is incorporated herein by reference.

GOVERNMENT CONTRACT

The U.S. Government has a paid-up license in this invention and the right and limited circumstances to require the patent owner to license others on reasonable terms as provided for by the terms of Contract No. DAMD17-95-2-5020 awarded by the U.S. Army Medical Research and Material Command of the U.S. Government.

BACKGROUND OF THE INVENTION

1. Field of the Invention

This invention generally relates to the field of telemedicine systems, and more particularly to a patient monitoring station comprised of a plurality of medical devices in communication with a single control unit.

2. Background Information

Traditional telemedicine systems are manufactured in a rigid manner with set numbers of medical devices packaged into a single product. Each medical device is connected to a computer with its own interface. This can be accomplished through the use of the standard serial ports on the computer and/or the addition of interface cards to support the devices. Each one of these ports and/or cards uses a single interrupt for each connected device.

Interrupts are commonly used to initiate real-time communication between a computer and a connected peripheral device. When a peripheral device has data to transmit to the computer, the device will generate a hardware interrupt to notify the computer of its request. An interrupt handler on the computer will detect the interrupt and dispatch an interrupt service routine (ISR) to process the interrupt. In general, interrupt requests are high priority events that result in suspension of the current running process on the computer to allow the ISR to run. In the event that multiple peripherals send interrupt request signals to the computer, a priority scheme can be implemented to determine the order in which the interrupts will be processed.

As discussed in the foregoing, current telemedicine systems use multiple interrupts and/or multiple cards and interfaces for multiple connected medical devices. Several problems are associated with this approach of using an interrupt for each medical device attached to a computer in a telemedicine system. Obviously, the total system cost and complexity is increased simply by using multiple cards. Additionally, the use of multiple cards reduces the number of available card slots in a computer, thereby limiting the number of additional cards and peripherals that can be attached to the computer. The addition of a new medical device often requires the installation of a new card, which can be time consuming. Finally, the number of medical devices that can be attached to a computer in a telemedicine system is limited to the number of available interrupts.

SUMMARY OF THE INVENTION

Certain objects, advantages and novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the advantages and novel features, the present invention is generally directed to a system and method that allow multiple medical devices to communicate with a control unit via a device interface that uses a single interrupt. Although not limited to these particular applications, the system and method are particularly suited to a patient monitoring station for use in a telemedicine system where numerous medical devices are connected to a personal computer.

In architecture, the patient monitoring station is implemented as follows. A plurality of medical devices are connected to a control unit via a device interface that uses a single interrupt. The device interface transmits data from the medical devices to the control unit. The patient monitoring station is configured so that the control unit and the medical devices can communicate with each other through the device interface. The device interface uses a single interrupt to request data transfer to the control unit.

In the present invention, the medical devices and control unit communicate with each other via the device interface. When the control unit has data to send, it transmits the data to the device interface along with the address of the medical device that is to receive the data. The device interface then decodes the address and transmits the data to the proper medical device. When a medical device has data to send to the control unit, it transmits the data to the device interface. The device interface then sends an interrupt request to the control unit via its single interrupt line. The control unit processes the interrupt request and the data is transmitted from the device interface to the control unit. A key feature of the present invention is the use of a device interface that uses a single interrupt in the transfer of data from multiple medical devices to a control unit rather than the use of separate interfaces and interrupts for every connected medical device.

The invention has numerous advantages, a few which are delineated, hereafter, as merely examples.

An advantage of the present invention is that it overcomes at least some of the problems and deficiencies of the prior art discussed hereinbefore.

Another advantage of the present invention is that it provides for the possibility of connecting a large number of medical devices to a single computer.

Another advantage of the present invention is that it reduces the complexity of the hardware associated with interrupt request generation and handling by using only a single interface.

Another advantage of the present invention is that it allows for easy interchangeability of connected medical devices.

Another advantage of the present invention is that it uses only one interface in a computer for all connected medical devices instead of an interface for each device, thereby providing resources for other peripherals.

Another advantage of the present invention is that it allows for plug and play compatibility with multiple medical devices.

Another advantage of the present invention is that it allows for the quick integration of new medical devices into the telemedicine system.

Other features and advantages of the invention will become apparent to one of ordinary skill in the art upon examination of the following drawings and detailed description. These additional features and advantages are intended to be included herein within the scope of the present invention.

BRIEF DESCRIPTION OF THE DRAWINGS

The present invention, as described in the claims, can be better understood with reference to the following drawings. The drawings are not necessarily to scale, emphasis instead being placed upon clearly illustrating principles of the present invention.

FIG. 4 is a flow chart of the transmission of data from the control unit to a medical device of FIG. 2.

FIG. 5 is a flow chart of the transmission of data from a medical device to the control unit of FIG. 2.

DESCRIPTION OF THE PREFERRED EMBODIMENT

Figure 1:
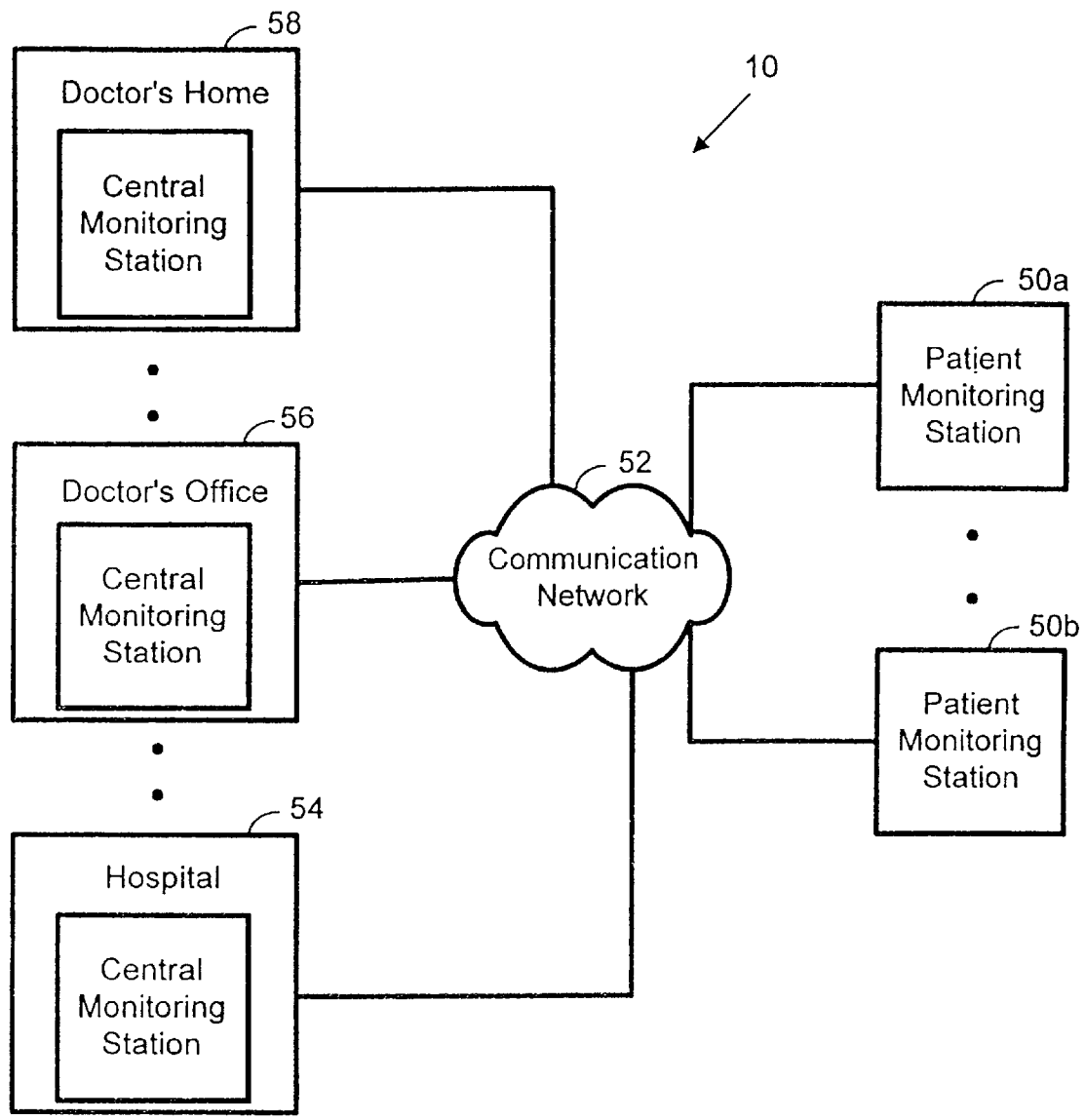
FIG. 1 is a block diagram of a telemedicine system comprising both patient monitoring stations and central monitoring stations.

Referring now to FIG. 1, a telemedicine system 10 is shown comprising a plurality of central monitoring stations 54, 56, 58 connected via communication network 52 to a plurality of patient monitoring stations 50a and 50b. As illustrated, a central monitoring station is provided at the hospital 54, the doctor's office 56 and the doctor's home 58. These locations for a central monitoring station are merely exemplary. In general, central monitoring stations will be placed in convenient and strategic locations for health care professionals to have remote access to their patients. Through any of these central monitoring stations 54, 56, 58, a health care professional can obtain diagnostic measurements performed on a patient at one of the remote patient monitoring stations 50a, 50b. Moreover, through communication network 52, the patient and the health care professional can communicate via any one or more combinations of voice, video and data.

Figure 2:
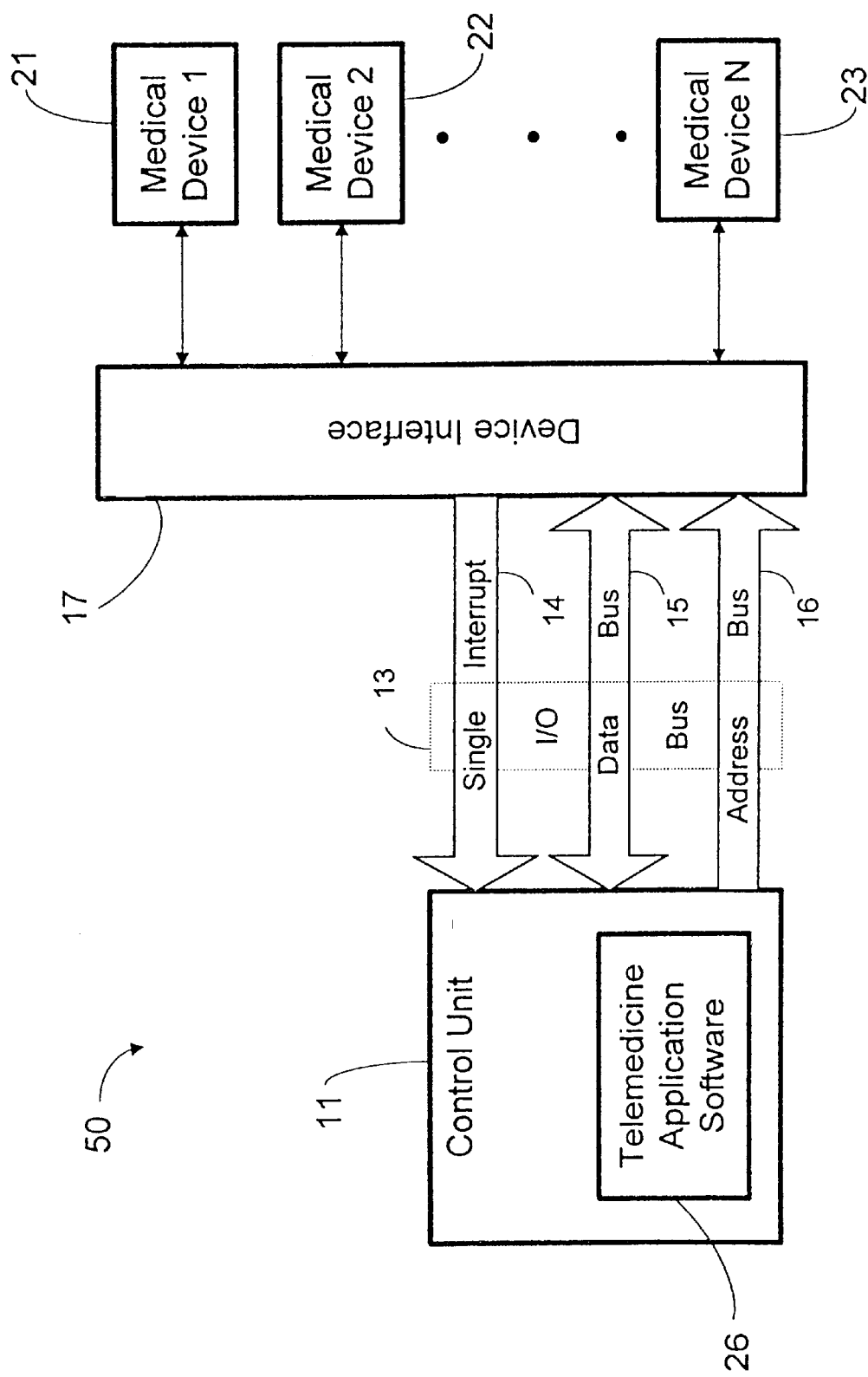
FIG. 2 is a block diagram of a patient monitoring station having N medical devices connected via a device interface having a single interrupt to a control unit.

The instant invention is directed towards patient monitoring station 50 as shown in FIG. 2, which is typically located in a remote (i.e., outside of a medical center) location such as a patient's home. The invention can be implemented in hardware or a combination of hardware and software. When implemented in a combination of hardware and software, the software supporting the single interrupt communication method for the patient monitoring station can be stored, transported, and/or utilized while residing on any computer readable medium for use by or in connection with any suitable computer based system. In the context of this document, a computer readable medium is an electronic, magnetic, optical, or other physical device or means that can contain or store a computer program for use by or in connection with a computer based system.

Figure 3:
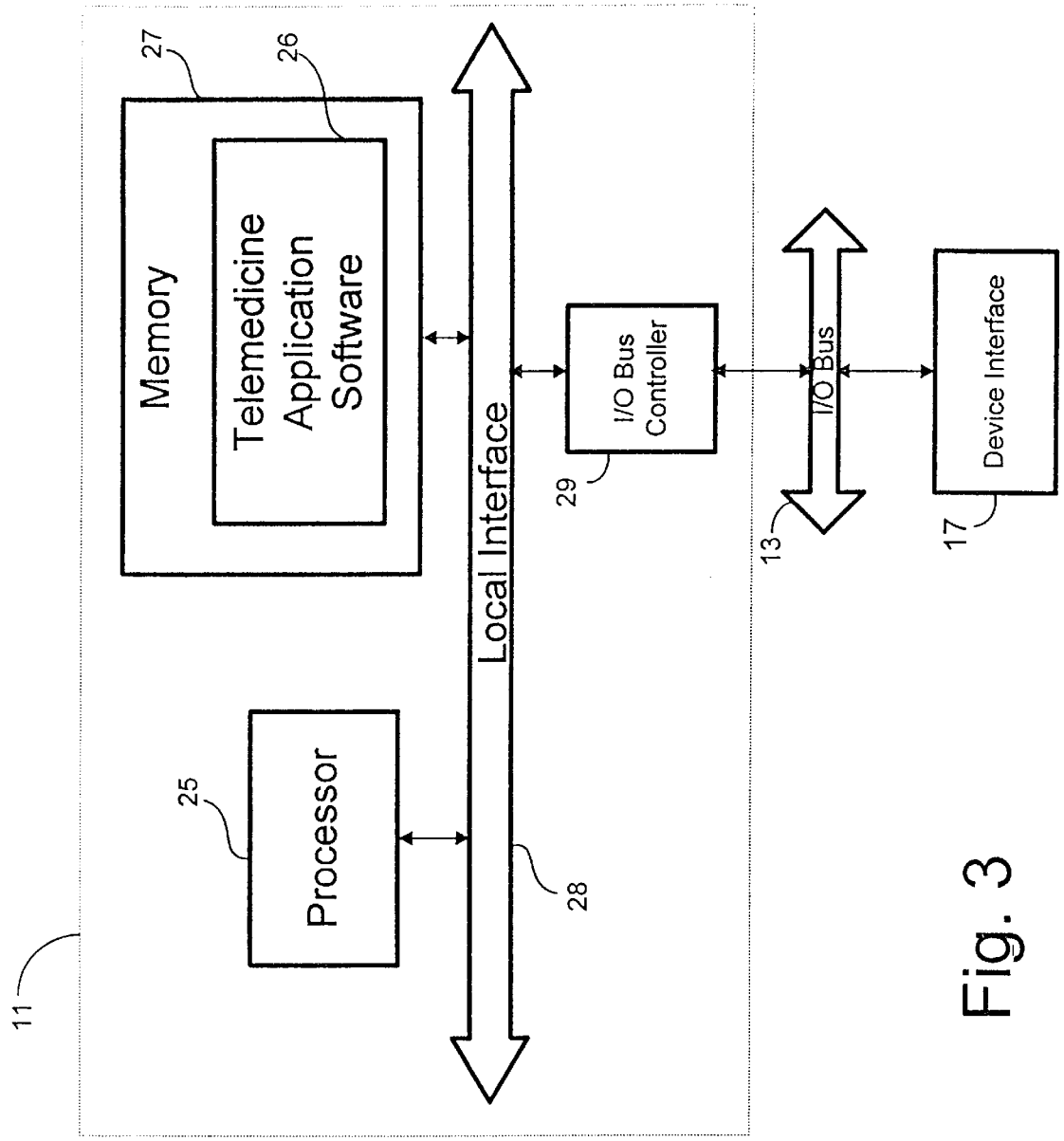
FIG. 3 is a block diagram of an embodiment of the control unit of FIG. 1.

A preferred architecture of the invention will now be described with reference to FIGS. 2 and 3. In general, FIG. 2 is a diagram of a patient monitoring station 50 having a control unit 11 connected to device interface 17 via I/O bus 13. I/O bus 13 is comprised of a data bus 15, address bus 16 and one or more interrupt lines of which only a single interrupt line 14 is used according to the instant invention. In the preferred embodiment, device interface 17 comprises a serial card that has multiple serial ports and, advantageously, uses only single interrupt line 14 to initiate communication with control unit 11, which is typically a personal computer. Device interface 17 is connected to a plurality of medical devices 21, 22, 23. Additional medical devices (not shown) may be configured to communicate with the same control unit 11 via device interface 17 or an additional interface (not shown) connected to the same control unit. FIG. 3 depicts an embodiment of the control unit 11 having the telemedicine application software 26 residing in memory 27 connected via a local interface or bus 28 to a processor 25.

As shown in FIG. 2, control unit 11 sends data to device interface 17 via a data bus 15 and address bus 16. Device interface 17 transmits the data placed on the data bus 15 to the appropriate medical device 21, 22, 23 by decoding the information placed on the address bus 16. The medical devices 21, 22, 23 transmit data to control unit 11 via device interface 17. In this process, one or more medical devices 21, 22, 23 sends data to device interface 17. Device interface 17 buffers and queues the requests and then uses single interrupt line 14 to indicate that it has data to transmit to control unit 11. Once control unit 11 is prepared to receive the data, device interface 17 sends the data to control unit 11 via data bus 15. Patient monitoring station 50 can contain one or more medical devices and one or more device interfaces connected to a single control unit.

Medical devices 21, 22, 23 can be implemented in numerous ways including, but not limited to, blood pressure devices, thermometers, pulse oximetry devices, electrocardiograms (EKGs), scales, stethoscopes, or any other diagnostic or data acquisition equipment. Additionally, medical devices can be freely interchanged with one another simply by unplugging one medical device from device interface 17 and plugging in another. This plug and play compatibility, made possible by the system configuration and use of a single interrupt interface, provides maximum flexibility in configuring patient monitoring station 50 to meet particular needs. Numerous combinations of different medical devices 21, 22, 23 can be used in patient monitoring station 50 via device interface 17. Device interface 17 can be implemented in numerous ways, including but not limited to, an RS232 interface, a single serial communications card, a bus such as the Firewire (IEEE 1394) or Universal Serial Bus (USB), or any other interface using a single interrupt in the data transfer process. Control unit 11 can also be implemented in numerous ways including, but not limited to, a personal computer or other type of processing unit.

One embodiment of control unit 11 is shown in FIG. 3. The processor 25 executes the telemedicine application software 26 which performs, among other tasks, the steps of the data transfer process. The processor 25 can include numerous methods for handling interrupts and processing interrupt requests. The device interface 17 can include numerous methods for converting data from medical devices 21, 22, 23 into a form comprehensible by control unit 11. The telemedicine application software 26 can include numerous methods for transmitting data destined for one or more medical devices 21, 22, 23 to device interface 17, converting data from a medical device 21, 22, 23 into a form comprehensible by control unit 11, converting data from device interface 17 into a form comprehensible by control unit 11, and/or facilitating communication between a medical device 21, 22, 23 and control unit 11 that use different protocols. In the preferred embodiment, the telemedicine application software 26 is stored in memory 27. Memory 27 can be implemented in numerous ways including, but not limited to, RAM, ROM, or any other memory device. The local interface 28 (e.g. one or more buses) connects the processor 25 and the memory 27 to I/O bus 13 via I/O bus controller 29 (see FIGS. 2 and 3). I/O bus 13 is typically an Industry Standard Architecture (ISA) or Peripheral Component Interconnect (PCI) bus.

The operation of the preferred embodiment of the telemedicine system 10 is described hereafter with reference to FIGS. 4 and 5. FIGS. 4 and 5 generally portray the steps in a transfer of data between a medical device 21, 22, 23 and control unit 11. In addition, FIGS. 4 and 5 provide an example of the operation of the single interrupt interface.

FIG. 4 depicts one possible combination of steps in the communications process whereby data is transferred from the control unit 11 to a medical device 21, 22, 23. In this context, device interface 17 is represented by a multiport serial interface card with one serial port connected to each medical device 21, 22, 23. The telemedicine application software 26 is initialized on control unit 1 and is executed by processor 25. This telemedicine application software 26 can include numerous routines used to process data resulting from an interrupt request. The first step of the data transfer process 31 occurs while the telemedicine application software 26 is running on control unit 11. In step 31, telemedicine application software 26 has data to send to one or more medical devices 21, 22, 23. Control unit 11, in step 33, places the address for the serial port corresponding to the medical device 21, 22, 23 to receive the data on the address bus 16, and the data is placed on the data bus 15. While the embodiment described herein uses a separate address and data bus, it should be apparent to one skilled in the art that a multiplexed or combined address/data bus could be used in the alternative. Device interface 17 decodes the address and enables the selected serial port corresponding to the requested medical device 21, 22, 23 in step 34. The selected serial port receives the data from the data bus 15 in step 35. Finally, the requested medical device 21, 22, 23 receives the data from device interface 17 over the selected serial port.

FIG. 5 illustrates one possible combination of steps in the communications process whereby data is transferred from a medical device 21, 22, 23 to control unit 11. In this context as well, device interface 17 is represented by a serial interface card with one serial port connected to each medical device 21, 22, 23. As before, the telemedicine application software 26 is running on control unit 11 during the transmission process. In step 41, one or more medical devices 21, 22, 23 sends data to device interface 17. Device interface 17 buffers and queues the data and then invokes an interrupt using the single interrupt line 14 in the next step 42. In step 43, the control unit 11 starts an interrupt service routine to handle the interrupt request. Numerous routines for processing the resulting data can be included in the telemedicine application software 26 or memory 27. In step 44, the interrupt service routine processes the interrupt and notifies the telemedicine application software 26 of the availability of the data in step 45. Finally, the telemedicine application software 26 reads the data sent originally by medical devices 21, 22, 23.

The device interface 17 can include numerous serial ports to handle data sent by multiple medical devices 21, 22, 23. In this manner, device interface 17 itself handles all data transfer, buffering, and priority functions associated with using a single interrupt. Inasmuch as numerous combinations of medical devices 21, 22, 23 can be connected to device interface 17, device interface 17 in conjunction with the telemedicine application software 26 provide a plug and play type of compatibility between the control unit 11 and the medical devices 21, 22, 23. Therefore, medical devices 21, 22, 23 can be connected and disconnected from device interface 17 in any combination. This feature of the single interrupt interface 17 and telemedicine application software 26 provides maximum flexibility in configuring patient monitoring station 50.

Additionally, the telemedicine application software 26 in conjunction with device interface 17 may perform necessary conversion or protocol translation functions. The telemedicine application software 26 includes routines for converting commands and/or data generated at a central monitoring station 54, 56, 58 (see FIG. 1) or by the telemedicine application software 26 itself at control unit 11 into a form comprehensible by one or more medical devices 21, 22, 23, that may use different communication protocols or data formats. This translation function facilitates the flow of information from central monitoring stations 54, 56, 58 through the telemedicine software 26 running on control unit 11 to a diverse set of medical devices 21, 22 and 23.

Similarly, the telemedicine application software 26 also performs the function of interpreting data received from medical devices 21, 22, 23 and formatting that information into a form suitable for transmission across communication network 52 for ultimate analysis at one or more central monitoring stations 54, 56, 58. Fundamentally, the telemedicine application software 26 includes protocol conversion and data translation routines necessary to facilitate communication between a central monitoring station and a patient monitoring station via communication network 52 and communication between control unit 11 and a diverse set of medical devices 21, 22, 23 within a patient monitoring station.

In concluding the detailed description, it should be noted that it will be obvious to those skilled in the art that many variations and modifications can be made to the preferred embodiment without substantially departing from the principles of the present invention. All such variations and modifications are intended to be included herein within the scope of the present invention, as set forth in the following claims. Further, in the claims hereafter, the corresponding structures, materials, acts, and equivalents of all means or step plus function elements are intended to include any structure, material, or acts for performing the functions with other claimed elements as specifically claimed.

We claim:

1. A patient monitoring system for use in a telemedicine system, comprising:

a plurality of medical devices;

a control unit;

a device interface connecting each of said medical devices to said control unit;

a first data bus connecting said control unit and said device interface;

an address bus connecting said control unit and said device interface;

a single interrupt connection connecting said control unit and said device interface;

a plurality of second data buses, each of which connects said device interface and a respective one of said medical devices;

wherein said device interface is designed to communicate data from said control unit to any one of said medical devices, said device interface being designed to communicate particular data from said control unit to a particular medical device by decoding an address corresponding to said particular medical device on said address bus in order to identify said particular medical device and by communicating said particular data received from said first data bus to a respective one of said second data buses that corresponds to said particular medical device;

wherein said device interface is designed to use a single interrupt in the transfer of data from said medical devices to said control unit, said device interface being designed to communicate data from any one of said medical devices to said control unit, said device interface designed to communicate certain data from a certain medical device to said control unit by receiving said certain data on a respective one of said second buses that is connected to said certain medical device, temporarily storing said certain data, communicating a single interrupt on said single interrupt connection to said control unit, and communicating said certain data received from said respective second data bus to said control unit via said first data bus.

2. The system of claim 1, wherein said medical devices are freely interchangeable with said device interface.

3. The system of claim 1, wherein said medical devices possess plug and play compatibility with said device interface.

4. The system of claim 1, wherein said interface is a single serial communications card having multiple serial ports for handling data transfer from a plurality of said medical devices and having a single interrupt interface with said control unit.

5. The system of claim 1, wherein said medical devices connect to said device interface via an RS232 interface.

6. The system of claim 1, wherein said control unit is a personal computer.

7. A patient monitoring system for use in a telemedicine system, comprising:

means for acquiring information about a patient's condition, said acquiring means comprising a plurality of medical devices;

means for controlling the acquisition of said information; and means for transferring said information from said acquiring means to said controlling means using a single interrupt, said transferring means comprising:
a first data bus means for connecting said controlling means and said acquiring means;
an address bus means for connecting said controlling means and said acquiring means;
a single interrupt connection means for connecting said controlling means and said acquiring means;
a plurality of second data bus means, each of which connects said transferring means and a respective one of said medical devices;

means for communicating data from any one of said medical devices to said controlling means by receiving said data on a respective one of said second bus means that is connected to said any medical device, communicating an interrupt on said single interrupt connection to said controlling means, and communicating said data received from said respective second data bus means to said controlling means via said first data bus means.

8. The system of claim 7, wherein said controlling means comprises a programmable control unit, said control unit being programmed to perform the following functions:
initiate the transmission of data from said acquiring means;
receive an interrupt on said control unit;
process data resulting from an interrupt service routine for said interrupt; and
transmit data to said acquiring means.

9. The system of claim 7, wherein said transferring means is a device interface.

10. A method of communication between a plurality of medical devices and a control unit using a single interrupt, comprising the steps of:
transmitting data from one of said medical devices to a device interface;
invoking an interrupt on said control unit with said device interface when any data is to be transferred from any one of said medical devices to said control unit by using a single interrupt request line for each and every one of said medical devices;
starting an interrupt service routine at said control unit for said interrupt; and
transmitting said data through said device interface to said control unit.

11. The method of claim 10 further comprising the step of converting said data from said medical devices into a format comprehensible by said control unit.

12. The method of claim 10, wherein said medical devices use a plurality of communication protocols for transmitting data and further comprising the step of translating between one of said communication protocols used by said medical devices and a communication protocol used by said control unit.

13. A programmable patient monitoring system for use in a telemedicine system, comprising:
a plurality of medical devices;
a programmable control unit;
a device interface connecting each of said medical devices to said control unit, said device interface using a single interrupt in the transfer of data from said medical devices to said control unit;
said control unit being programmed to perform the following functions:
initiate the transmission of data from one of said medical devices to said device interface;
receive an interrupt on said control unit;
process data resulting from an interrupt service routine for said interrupt; and
transmit data to said medical devices through said device interface.

14. The system of claim 13, wherein said interface is a single serial communications card having multiple serial ports for handling data transfer from a plurality of said medical devices and having a single interrupt interface with said control unit.

15. The system of claim 13, wherein said medical devices connect to said device interface via an RS232 interface.

16. The system of claim 7, wherein said transferring means further comprises a means for communicating data from said controlling means to any one of said medical devices, for communicating particular data from said controlling means to a particular medical device by decoding an address corresponding to said particular medical device on said address bus means in order to identify said particular medical device and by communicating said particular data received from said first data bus means to a respective one of said second data bus means that corresponds to said particular medical device.

17. The system of claim 7, wherein said medical devices are freely interchangeable with said device interface.

18. The system of claim 7, wherein said medical devices possess plug and play compatibility with said device interface.

19. The system of claim 7, wherein said acquiring means is a single serial communications card having multiple serial ports for handling data transfer from a plurality of said medical devices and having a single interrupt interface with said controlling means.

20. The system of claim 7, wherein said medical devices connect to said transferring means via an RS232 interface.

21. The method of claim 10, further comprising the steps of:

communicating data from said control unit to any one of said medical devices;

communicating particular data from said control unit to a particular medical device by decoding an address corresponding to said particular medical device at said device interface in order to identify said particular medical device and by communicating said particular data to said particular medical device through said device interface.

22. The method of claim 10, wherein said medical devices are freely interchangeable with said device interface.

23. The method of claim 10, wherein said medical devices possess plug and play compatibility with said device interface.

24. The method of claim 10, wherein said acquiring means is a single serial communications card having multiple serial ports for handling data transfer from a plurality of said medical devices and having a single interrupt interface with said controlling means.

25. The method of claim 10, wherein said medical devices connect to said transferring means via an RS232 interface.

* * * * *

UNITED STATES PATENT AND TRADEMARK OFFICE
CERTIFICATE OF CORRECTION

PATENT NO. : 6,112,224
DATED : August 29, 2000
INVENTOR(S) : Peifer, et al.

Page 1 of 1

It is certified that error appears in the above-identified patent and that said Letters Patent is hereby corrected as shown below:

Title Page,
Item [56] Reference Cited, add the U.S. Patent Document -- 5,640,953; 06/1997; Bishop et al.; 128/630 --.

Column 2,
Line 45, after the word "few" add the word -- of --.

Column 5,
Line 25, after the word "unit", delete the numeral "1", and substitute therefor -- 11 --.

Claims,
Column 7,
Line 31, after the word "said", add the word -- device --.

Column 8,
Line 2, after the word "said", add the word -- programmable --.

Column 10,
Lines 13 and 14, after the word "said", delete the phrase "aquiring means", and substitute therefor -- device interface --.

Signed and Sealed this

Twenty-third Day of October, 2001

Attest:

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO. : 6,112,224
DATED : August 29, 2000
INVENTOR(S) : Peifer, et al.

Page 1 of 1

It is certified that error appears in the above-identified patent and that said Letters Patent is hereby corrected as shown below:

Title page,
Item [56] Reference Cited, add the U.S. Patent Document -- 5,640,953; 06/1997; Bishop et al.; 128/630 --.

Column 2,
Line 45, after the word "few" add the word -- of --.

Column 5,
Line 25, after the word "unit", delete the numeral "1", and substitute therefor -- 11 --.

Claims,
Column 7,
Line 31, after the word "said", add the word -- device --.

Column 8,
Line 2, after the word "said", add the word -- programmable --.

Column 10,
Lines 13 and 14, after the word "said", delete the phrase "acquiring means", and substitute therefor -- device interface --.

Signed and Sealed this

Thirteenth Day of November, 2001

Attest:

*Nicholas P. Godici*

NICHOLAS P. GODICI
*Attesting Officer*   *Acting Director of the United States Patent and Trademark Office*